United States Patent
Benni

(10) Patent No.: US 11,363,976 B2
(45) Date of Patent: **\*Jun. 21, 2022**

(54) METHOD FOR SPECTROPHOTOMETRIC BLOOD OXYGENATION MONITORING OF ORGANS IN THE BODY

(71) Applicant: Edwards Lifesciences Corporation, Irvine, CA (US)

(72) Inventor: Paul B. Benni, Acton, MA (US)

(73) Assignee: Edwards Lifesciences Corporation, Irvine, CA (US)

( * ) Notice: Subject to any disclaimer, the term of this patent is extended or adjusted under 35 U.S.C. 154(b) by 224 days.

This patent is subject to a terminal disclaimer.

(21) Appl. No.: 16/692,863

(22) Filed: Nov. 22, 2019

(65) Prior Publication Data

US 2020/0085359 A1 Mar. 19, 2020

Related U.S. Application Data

(60) Continuation of application No. 15/172,992, filed on Jun. 3, 2016, now Pat. No. 10,485,462, which is a (Continued)

(51) Int. Cl.
*A61B 5/1455* (2006.01)
*A61B 5/00* (2006.01)

(52) U.S. Cl.
CPC ........ *A61B 5/14551* (2013.01); *A61B 5/4836* (2013.01); *A61B 5/4848* (2013.01); (Continued)

(58) Field of Classification Search
CPC .............. A61B 5/1455; A61B 5/14551; A61B 5/14552; A61B 5/7271; A61B 2562/0233
See application file for complete search history.

(56) References Cited

U.S. PATENT DOCUMENTS 6,766,188 B2 7/2004 Soller
7,010,337 B2 3/2006 Furnary et al.
(Continued)

FOREIGN PATENT DOCUMENTS

EP 0352923 A1 1/1990

OTHER PUBLICATIONS

Ho et al., "In Vivo Detection of Myocardial Ischemia in Pigs Using Visible Light Spectroscopy," Anethesia and Analgesia, vol. 108, No. 4, Apr. 1, 2009, pp. 1185-1192.
(Continued)

*Primary Examiner* — Eric F Winakur
(74) *Attorney, Agent, or Firm* — Richard D. Getz; Getz Balich

(57) ABSTRACT

A method and apparatus for non-invasively determining a blood oxygen saturation level within tissue of an internal organ is provided. The method includes: applying a near infrared spectrophotometric sensor on an external surface of an organ; operating the sensor to emit light from a light source directly into the tissue of the organ at a first tissue location, and to sense the emitted light at a second tissue location, which emitted light has traveled through the tissue between the first and second tissue locations, and to produce signals representative of the intensity of the sensed emitted light; using a processor to execute instructions, which instructions cause the processor to: determine an attenuation value of the emitted light for each wavelength, and determine a blood oxygen saturation level of the organ tissue using the determined attenuation values for each of the plurality of wavelengths.

9 Claims, 4 Drawing Sheets

Related U.S. Application Data division of application No. 13/511,928, filed as application No. PCT/US2010/058059 on Nov. 24, 2010, now Pat. No. 9,364,175.

(60) Provisional application No. 61/264,080, filed on Nov. 24, 2009.

(52) U.S. Cl.
CPC .......... *A61B 5/7246* (2013.01); *A61B 5/7271* (2013.01); *A61B 5/7278* (2013.01); *A61B 5/746* (2013.01); *A61B 2562/0233* (2013.01)

(56) References Cited

U.S. PATENT DOCUMENTS

| | | |
|---|---|---|
| 7,123,950 B2 | 10/2006 | Mannheimer |
| 2001/0047128 A1 | 11/2001 | Benni |
| 2004/0024297 A1 | 2/2004 | Chen et al. |
| 2004/0073278 A1 | 4/2004 | Pachys |
| 2004/0082841 A1 | 4/2004 | Furnary et al. |
| 2006/0034941 A1 | 2/2006 | Dobson |
| 2006/0167400 A1 | 7/2006 | Ellingboe et al. |
| 2007/0265513 A1 | 11/2007 | Schenkman et al. |
| 2008/0200780 A1 | 8/2008 | Schenkman et al. |
| 2009/0182209 A1 | 7/2009 | Benni |

OTHER PUBLICATIONS

Kawasuji et al., "Near-Infrared Monitoring of Myocardial Oxygenation During Intermittent Warm Blood Cardioplegia," European Journal of Cardio-Thoracic Surgery, vol. 12, No. 2, Aug. 1, 1997, pp. 236-241.

METHOD FOR SPECTROPHOTOMETRIC BLOOD OXYGENATION MONITORING OF ORGANS IN THE BODY

This application is a continuation of U.S. patent application Ser. No. 15/172,992 filed Jun. 3, 2016, which is a divisional of U.S. patent application Ser. No. 13/511,928, now U.S. Pat. No. 9,364,175, filed Oct. 4, 2012, which is a national stage application of PCT Patent Application No. PCT/US2010/058059 filed on Nov. 24, 2010, which claims priority to U.S. Provisional Patent Application No. 61/264,080 filed Nov. 24, 2009, the disclosures of which are herein incorporated by reference.

BACKGROUND OF THE INVENTION

1. Technical Field

This invention relates to methods for non-invasively determining biological tissue oxygenation in general, and to non-invasive methods utilizing near-infrared spectroscopy (NIRS) techniques in particular.

2. Background Information

Oxygen saturation in a mammalian subject can be defined as:

$$O_2 \text{ saturation \%} = \frac{HbO_2}{(HbO_2 + Hb)} * 100\% \quad \text{(Eqn.1)}$$

where $HbO_2$ refers to oxygenated hemoglobin (i.e., "oxyhemoglobin") and Hb refers to deoxygenated hemoglobin (i.e., "deoxyhemoglobin"). In the arterial circulatory system under normal conditions, there is a high proportion of $HbO_2$ to Hb, resulting in an arterial oxygen saturation (defined as $SaO_2\%$) of 95-100%. After delivery of oxygen to tissue via the capillaries, the proportion of $HbO_2$ to Hb decreases. Therefore, the measured oxygen saturation of venous blood (defined as $SvO_2\%$) is lower and may be about 70%.

One spectrophotometric method, called pulse oximetry, determines arterial oxygen saturation ($SaO_2$) of peripheral tissue (i.e. finger, ear, nose) by monitoring pulsatile optical attenuation changes of detected light induced by pulsatile arterial blood volume changes in the arteriolar vascular system. The method of pulse oximetry requires pulsatile blood volume changes in order to make a measurement. Since venous blood is not pulsatile, pulse oximetry cannot provide any information about venous blood.

Near-infrared spectroscopy (NIRS) is an optical spectrophotometric method of continually monitoring tissue oxygenation that does not require pulsatile blood volume to calculate parameters of clinical value. The NIRS method utilizes light in the near-infrared range (700 to 1,000 nm) that can pass easily through skin, bone and other tissues where it encounters hemoglobin located mainly within micro-circulation passages; e.g., capillaries, arterioles, and venuoles. Hemoglobin exposed to light in the near infra-red range has specific absorption spectra that varies depending on its oxidation state; i.e., oxyhemoglobin ($HbO_2$) and deoxyhemoglobin (Hb) each act as a distinct chromophore. By using light sources that transmit near-infrared light at specific different wavelengths, and measuring changes in transmitted or reflected light attenuation, concentration changes of the oxyhemoglobin ($HbO_2$) and deoxyhemoglobin (Hb) can be monitored.

The apparatus used in NIRS analysis typically includes a plurality of light sources, one or more light detectors for detecting reflected or transmitted light, and a processor for processing signals that represent the light emanating from the light source and the light detected by the light detector. Light sources such as light emitting diodes (LEDs) or laser diodes that produce light emissions in the wavelength range of 700-1000 nm at an intensity below that which would damage the biological tissue being examined are typically used. A photodiode or other light source detector is used to detect light reflected from or passed through the tissue being examined. The processor takes the signals from the light sources and the light detector and analyzes those signals in terms of their intensity and wave properties.

It is known that relative changes of the concentrations of $HbO_2$ and Hb can be evaluated using apparatus similar to that described above, including a processor programmed to utilize a variant of the Beer-Lambert Law, which accounts for optical attenuation in a highly scattering medium like biological tissue. The modified Beer-Lambert Law can be expressed as:

$$A_\lambda = -\log(I/I_o)_{80} = \alpha_{80} * C * d * B_\lambda + G \quad \text{(Eqn. 2)}$$

wherein "$A_\lambda$" represents the optical attenuation in tissue at a particular wavelength λ (units: optical density or OD); "$I_o$" represents the incident light intensity (units: $W/cm^2$); "I" represents the detected light intensity; "$\alpha_\lambda$" represents the wavelength dependent absorption coefficient of the chromophore (units: $OD*cm^{-1}*\mu M^{-1}$); "C" represents the concentration of chromophore (units: μM); "d" represents the light source to detector (optode) separation distance (units: cm); "$B_\lambda$" represents the wavelength dependent light scattering differential pathlength factor (unitless); and "G" represents light attenuation due to scattering within tissue (units:OD). The product of "$d*B_\lambda$" represents the effective pathlength of photon traveling through the tissue.

Absolute measurement of chromophore concentration (C) is very difficult because G is unknown or difficult to ascertain. However, over a reasonable measuring period of several hours to days, G can be considered to remain constant, thereby allowing for the measurement of relative changes of chromophore from a zero-reference baseline. Thus, if time $t_1$ marks the start of an optical measurement (i.e., a base line) and time $t_2$ is an arbitrary point in time after $t_1$, a change in attenuation (ΔA) between $t_1$ and $t_2$ can be calculated, and variables G and $I_o$ will cancel out providing that they remain constant.

The change in chromophore concentration (ΔC=C($t_2$)−C($t_1$)) can be determined from the change in attenuation ΔA, for example using the following equation derived from the modified Beer-Lambert Law:

$$\Delta A_\lambda = -\log(I_{t2}/I_{t1})_\lambda = \alpha_\lambda * \Delta C * d * B_\lambda \quad \text{(Eqn. 3)}$$

Presently known NIRS algorithms that are designed to calculate the relative change in concentration of more than one chromophore use a multivariate form of Equation 2 or 3. To distinguish between, and to compute relative concentration changes in, oxyhemoglobin ($\Delta HbO_2$) and deoxyhemoglobin (ΔHb), a minimum of two different wavelengths are typically used. The concentration of the $HbO_2$ and Hb within the examined tissue is determined in μmoles per liter of tissue (μM).

The above-described NIRS approach to determining oxygenation levels is useful, but it is limited in that it only provides information regarding a change in the level of oxygenation within the tissue. It does not provide a means for determining the absolute value of oxygen saturation within the biological tissue.

At present, information regarding the relative contributions of venous and arterial blood within tissue examined by NIRS is either arbitrarily chosen or is determined by invasive sampling of the blood as a process independent from the NIRS examination. For example, it has been estimated that NIRS examined brain tissue comprising about 60 to 80% blood venous and about 20 to 40% arterial blood. Blood samples from catheters placed in venous drainage sites such as the internal jugular vein, jugular bulb, or sagittal sinus have been used to evaluate NIRS measurements. Results from animal studies have shown that NIRS interrogated tissue consists of a mixed vascular bed with a venous-to-arterial ratio of about 2:1 as determined from multiple linear regression analysis of sagittal sinus oxygen saturation ($SssO_2$) and arterial oxygen saturation ($SaO_2$). An expression representing the mixed venous/arterial oxygen saturation ($SmvO_2$) in NIRS examined tissue is shown by the equation:

$$SmvO_2 = Kv*SvO_2 + Ka*SaO_2 \qquad (Eqn.\ 4)$$

where "$SvO_2$" represents venous oxygen saturation; "$SaO_2$" represents arterial oxygen saturation; and Kv and Ka are the weighted venous and arterial contributions respectively, with Kv+Ka=1. The parameters Kv and Ka may have constant values, or they may be a function of $SvO_2$ and $SaO_2$. Determined oxygen saturation from the internal jugular vein ($SijvO_2$), jugular bulb ($SjbO_2$), or sagittal sinus ($SssO_2$) can be used to represent $SvO_2$. Therefore, the value of each term in Equation 4 is empirically determined, typically by discretely sampling or continuously monitoring and subsequently evaluating patient arterial and venous blood from tissue that the NIRS sensor is examining, and using regression analysis to determine the relative contributions of venous and arterial blood independent of the NIRS examination.

Some medical procedures involve limiting or completely stopping the flow of blood to an organ. For example, some procedures involve isolating the heart from the rest of the body by means of a cross clamp on the aorta and then cold cardioplegia is given into the heart through the aortic root. The cold fluid (usually in the range of about 4-10° C.) ensures that the heart cools down to an approximate temperature of around 15-20° C. thus slowing down the metabolism of the heart and thereby preventing damage to the heart muscle. The process may be further augmented by a cardioplegic component which is high in potassium and magnesium. The potassium helps by arresting the heart in diastole thus ensuring that the heart does not use up the valuable energy stores during this period of heart isolation. Blood can be added to this solution especially for long procedures requiring more than half an hour of ascending aorta cross-clamp time. Blood acts as a buffer and also supplies nutrients to the heart during ischemia. Once the procedure on the heart vessels (e.g., coronary artery bypass grafting, or heart valve replacement, or correction of congenital heart defect, etc.) is over, the cross-clamp is removed and the isolation of the heart is terminated so that normal blood supply to the heart is restored and the heart starts beating again.

During the isolation period, it would be of great value to monitor the oxygen saturation level of the heart to ensure that the heart has a sufficient oxygen level to avoid damage. The cessation of blood flow to an organ is not limited to hearts, however. For example, livers and kidneys are often removed from a donor for transplant into a recipient. In such cases, there would be value in knowing the oxygen saturation level in the organ before, during, and after the transplant.

What is needed, therefore, is a method for non-invasively determining the level of oxygen saturation within biological tissue that can determine the absolute oxygen saturation value rather than a change in level, and one that can be used to directly determine the oxygen saturation levels of a body organ.

DISCLOSURE OF THE INVENTION

According to an aspect of the present invention, a method and apparatus for non-invasively determining a blood oxygen saturation level within an organ of a subject using direct application of a near infrared spectrophotometric sensor is provided. The method includes the steps of: a) transmitting a light signal directly into the subject's organ using the sensor along multiple wavelengths; b) sensing a first intensity of the light signal and a second intensity of the light signal, after the light signal travels a predetermined distance through the organ of the subject; c) determining an attenuation of the light signal along multiple third wavelengths using the sensed first intensity and sensed second intensity of wavelengths; d) determining a difference in attenuation of the light signal between multiple wavelengths; and e) determining the blood oxygen saturation level within the subject's organ using the difference in attenuation between the multiple wavelengths.

According to another aspect of the present invention, an apparatus for non-invasively determining a blood oxygen saturation level within an organ of a subject is provided. The apparatus includes at least one near infrared spectrophotometric sensor operable to be placed in contact with the organ, and a processor. The sensor has at least one light source and at least one light detector. The light source is operable to transmit a light signal that includes a first wavelength, a second wavelength, and a third wavelength. The light detector is operable to sense the light signal along the first, second, and third wavelengths after the light signal travels a predetermined distance through the organ tissue. The sensor is operable to produce data signals representative of the sensed light signal. The processor is adapted to receive the data signals from the sensor, and is adapted to determine an attenuation of the light signal for each of the first, second, and third wavelengths. The processor is further adapted to determine the blood oxygen saturation level within the organ tissue using the difference in attenuation.

According to another aspect of the present invention, a method for regulating a tissue oxygenation level within a mammalian organ is provided. The method includes the steps of: a) providing an organ tissue oxygenation level threshold; b) applying a near infrared spectrophotometric sensor onto a region of the organ, which sensor is in communication with a processor adapted to receive data signals from the sensor, and is adapted to determine the oxygen saturation level within the organ tissue using the data signals; c) sensing the oxygen saturation level within the organ tissue using the spectrophotometric sensor, and producing a sensed organ tissue oxygenation level value using the processor; d) comparing the organ tissue oxygenation level threshold and the sensed organ tissue oxygenation level value; and e) selectively treating the organ to increase the tissue oxygenation level within the organ based on the comparison.

According to another aspect of the present invention, a method for monitoring the effects of cardioplegia administered to a heart is provided. The method includes the steps of: a) applying a near infrared spectrophotometric sensor onto a region of the heart, which sensor is in communication with a processor adapted to receive data signals from the sensor, and is adapted to determine the oxygen saturation level within heart tissue using the data signals; b) sensing the oxygen saturation level within the heart tissue using the spectrophotometric sensor before an administration of a cardioplegia to the heart, and producing a pre-administration sensed heart tissue oxygenation level value using the processor; c) administering a cardioplegia to the heart; and d) sensing the oxygen saturation level within the heart tissue using the spectrophotometric sensor after the administration of the cardioplegia to the heart, and producing a post-administration sensed heart tissue oxygenation level value using the processor.

These and other objects, features, and advantages of the present invention method and apparatus will become apparent in light of the detailed description of the invention provided below and the accompanying drawings. The methodology and apparatus described below constitute a preferred embodiment of the underlying invention and do not, therefore, constitute all aspects of the invention that will or may become apparent by one of skill in the art after consideration of the invention disclosed overall herein.

DETAILED DESCRIPTION THE INVENTION

Figure 1:
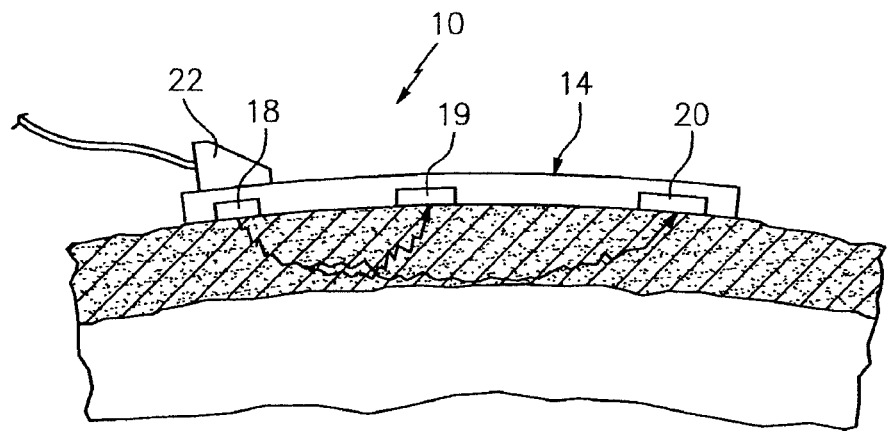
FIG. 1 is a diagrammatic side representation of a NIRS sensor disposed on the surface of an organ.
Figure 2:
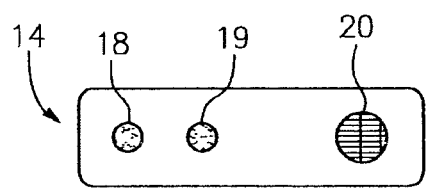
FIG. 2 is a diagrammatic planar view of a NIRS sensor.
Figure 3:
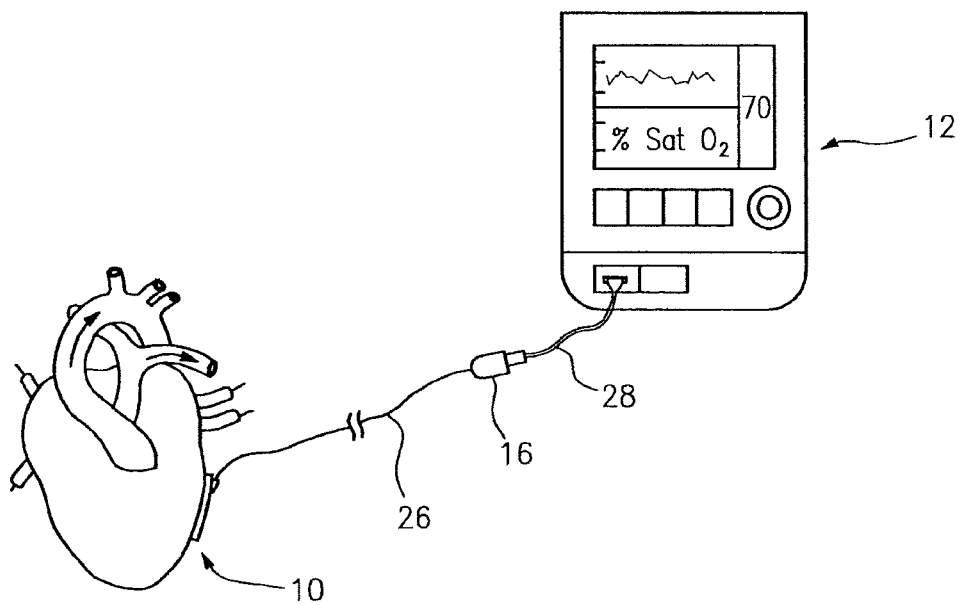
FIG. 3 is a diagrammatic representation of a NIRS system, including a sensor placed on an organ of a subject.
Figure 4:
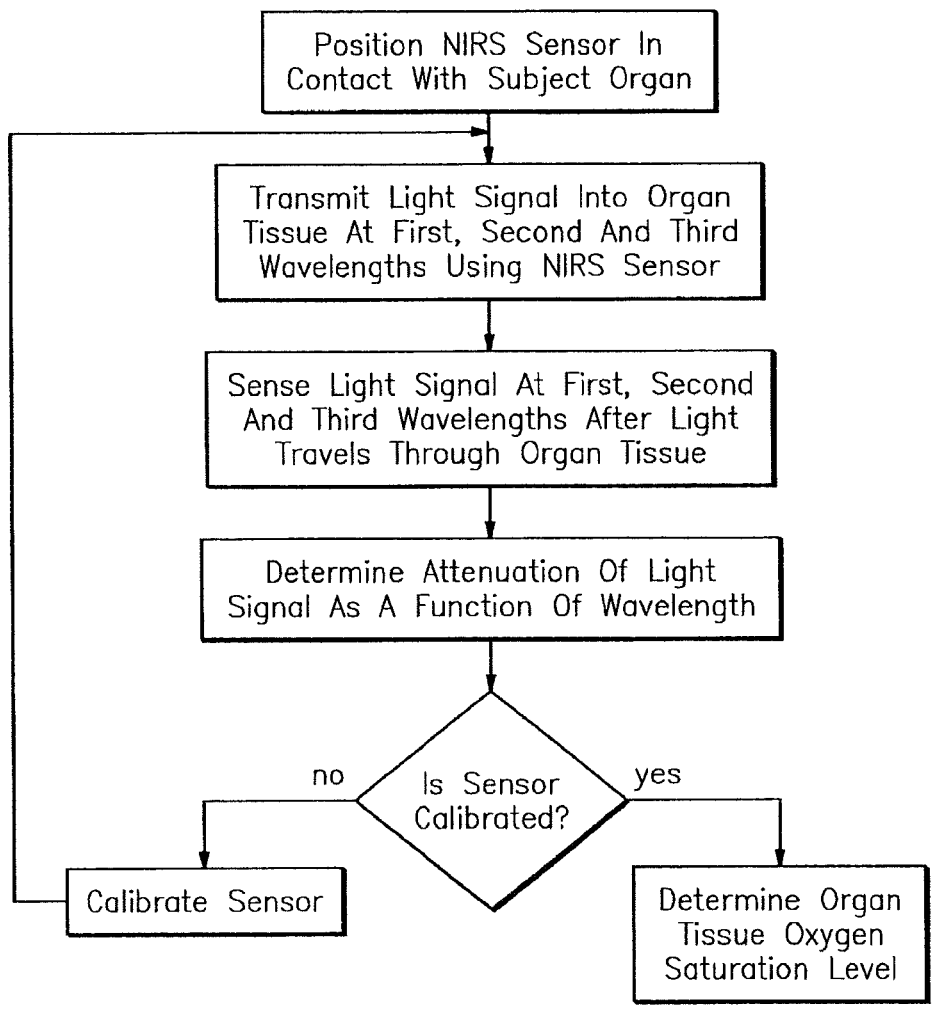
FIG. 4 is a block diagram of the present methodology.
Figure 5:
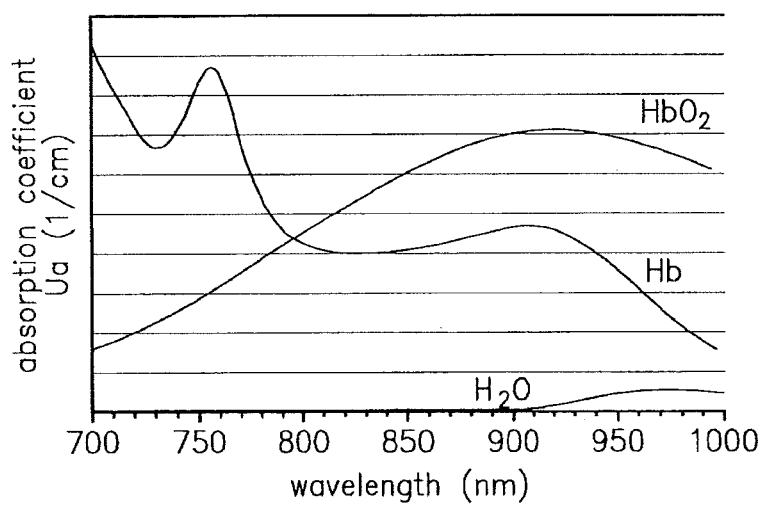
FIG. 5 is a graph showing an exemplary plot of absorption coefficient vs. wavelength.

The present method of and apparatus for non-invasively determining the blood oxygen saturation level within a subject's tissue is provided that utilizes a near infrared spectrophotometric (NIRS) sensor that includes a transducer capable of transmitting a light signal into the tissue of a subject and sensing the light signal once it has passed through the tissue via transmittance or reflectance. The present method and apparatus can be used with a variety of NIRS sensors. The present method is not limited to use with this preferred NIRS sensor, however.

Referring to FIGS. 1-5, the preferred NIRS sensor includes a transducer portion 10 and processor portion 12. The transducer portion 10 includes an assembly housing 14 and a connector housing 16. The assembly housing 14, which is a flexible structure that can be attached directly to a subject's body, includes one or more light sources 18 and one or more light detectors 19, 20. A sterile disposable envelope or pad may be used to mount the assembly housing 14 to the subject's skin or organ. Light signals of known but different wavelengths from the light sources 18 emit through a prism assembly 22. The light sources 18 are preferably laser diodes that emit light at a narrow spectral bandwidth at predetermined wavelengths. Alternative light emitting diodes (LEDs) can be used if the algorithm is drafted to consider the LEDs characteristic broad spectral bandwidth emitted light. In one embodiment, the laser diodes are mounted within the connector housing 16. The laser diodes are optically interfaced with a fiber optic light guide to the prism assembly 22 that is disposed within the assembly housing 14. In a second embodiment, the light sources 18 are mounted within the assembly housing 14. A first connector cable 26 connects the assembly housing 14 to the connector housing 16 and a second connector cable 28 connects the connector housing 16 to the processor portion 12. The light detectors 19, 20 each include one or more photodiodes, which are operably connected to the processor portion 12 via the first and second connector cables 26, 28. The processor portion 12 includes a processor for processing light intensity signals from the light sources 18 and one or both light detectors 19, 20.

The processor 12 includes a central processing unit (CPU) and is adapted (e.g., programmed) to selectively perform the functions necessary to perform the present method. It should be noted that the functionality of processor 12 may be implemented using hardware, software, firmware, or a combination thereof. A person skilled in the art would be able to program the processor 12 to perform the functionality described herein without undue experimentation. The processor 12 utilizes an algorithm that characterizes a change in attenuation as a function of the difference in attenuation between different wavelengths. In some embodiments, the present method accounts for but minimizes the effects of pathlength and parameter "E", that latter of which represents energy losses (i.e. light attenuation) due to light scattering within tissue (G), other background absorption losses from biological compounds (F), and other unknown losses including measuring apparatus variability (N). E=G+F+N. Multi-tissue layer organs such as the kidney benefit from multi-detector NIRS sensors and algorithms. In some embodiments, an alternative algorithm may be used that considers fewer or different energy loss components; e.g., if a subject heart is being directly sensed for oxygen saturation, an alternative algorithm may be used that recognizes the absence of certain types of tissue (e.g., skin, bone, etc.) and the signal energy losses associated therewith.

Refer to FIG. 1, the absorption $A_{b\lambda}$ detected from the deep light detector 20 comprises of attenuation and energy loss from both the deep and shallow tissue, while the absorption $A_{x\lambda}$ detected from the shallow light detector 19 comprises of attenuation and energy loss from shallow tissue only. Absorptions $A_{b\lambda}$ and $A_{x\lambda}$ can be expressed in the form of Equation 5 and Equation 6 below which is a modified version of Equation 2 that accounts for energy losses due to "E":

$$A_{b\lambda} = -\log(I_b/I_o)_\lambda = \alpha_\lambda * C_b * L_b + \alpha_\lambda * C_x * L_x + E_\lambda \quad \text{(Eqn. 5)}$$

$$A_{x\lambda} = -\log(I_x/I_o)_\lambda = \alpha_\lambda * C_x * L_x + E_{x\lambda} \quad \text{(Eqn. 6)}$$

As indicated above, in some applications (e.g., direct organ sensing, where the signal does not traverse skin or bone) it may be possible to sense using a sensor with a single detector. In those instances, the following equation can used to represent absorption:

$$A_{b\lambda} = -\log(I_b/I_o)_\lambda = \alpha_\lambda * C_b * L_b + E_\lambda \quad \text{(Eqn. 7)}$$

Substituting Equation 6 into Equation 5 yields $A'_\lambda$, which represents attenuation and energy loss from deep tissue only:

$$A'_\lambda = A_{b\lambda} - A_{x\lambda} = \alpha_\lambda * C_b * L_b + (E_\lambda - E_{x\lambda}) = -\log\left(\frac{I_b}{I_x}\right)_\lambda \quad \text{(Eqn. 8)}$$

Where L is the effective pathlength of the photon traveling through the deep tissue and $A'_1$ and $A'_2$, are the absorptions of two different wavelengths. Let $E'_\lambda = E_\lambda - E_{x\lambda}$, therefore:

$$A'_1 - A'_2 = \Delta A'_{12} \quad \text{(Eqn. 9)}$$

Substituting Equation 7 or 8 into Equation 9 for $A'_1$ and $A'_2$, $\Delta A'_{12}$ can be expressed as:

$$\Delta A'_{12} = \alpha_{\lambda 12} * C_b * L_b + \Delta E'_{12} \quad \text{(Eqn. 10)}$$

and rewritten Equation 10 in expanded form:

$$\Delta A'_{12} = \langle(\alpha_{r1} - \alpha_{r2})[Hb]_b + (\alpha_{o1} - \alpha_{o2})[HbO_2]_b\rangle L_b + (E'_1 - E'_2) = \quad \text{(Eqn. 11)}$$
$$(\Delta\alpha_{r12} * [Hb]_b * L_b) + (\Delta\alpha_{o12} * [HbO_2]_b * L_b) + \Delta E'_{12}$$

where:

$(\Delta\alpha_{r12} * [Hb]_b * L_b)$ represents the attenuation attributable to Hb;

$(\Delta\alpha_{o12} * [HbO_2]_b * L_b)$ represents the attenuation attributable to $HbO_2$; and $\Delta E'_{12}$ represents energy losses (i.e. light attenuation) due to light scattering within tissue, other background absorption losses from biological compounds, and other unknown losses including measuring apparatus variability. As indicated above, the specific energy losses accounted for can be varied to suit the application at hand; e.g., inclusion or exclusion of energy losses attributable to skin and bone, use of a single detector versus a pair of detectors, etc.

The multivariate form of Equation 10 is used to determine $[HbO_2]_b$ and $[Hb]_b$ with three different wavelengths:

$$\begin{bmatrix} \Delta A'_{12} - \Delta E'_{12} \\ \Delta A'_{13} - \Delta E'_{13} \end{bmatrix}(L_b)^{-1} = \begin{bmatrix} \Delta\alpha_{r12} & \Delta\alpha_{o12} \\ \Delta\alpha_{r13} & \Delta\alpha_{o13} \end{bmatrix}\begin{bmatrix} [Hb]_b \\ [HbO_2]_b \end{bmatrix} \quad \text{(Eqn. 12)}$$

Rearranging and solving for $[HbO_2]_b$ and $[Hb]_b$, simplifying the $\Delta\alpha$ matrix into $[\Delta\alpha']$:

$$\begin{bmatrix} \Delta A'_{12} \\ \Delta A'_{13} \end{bmatrix}[\Delta\alpha']^{-1}(L_b)^{-1} - \begin{bmatrix} \Delta E'_{12} \\ \Delta E'_{13} \end{bmatrix}[\Delta\alpha']^{-1}(L_b)^{-1} = \begin{bmatrix} [Hb]_b \\ [HbO_2]_b \end{bmatrix} \quad \text{(Eqn. 13)}$$

Then combined matrices $[\Delta A'][\Delta\alpha']^{-1} = [A_c]$ and $[\Delta E][\Delta\alpha']^{-1} = [\Psi_c]$:

$$\begin{bmatrix} A_{Hb} \\ A_{HbO_2} \end{bmatrix}(L_b)^{-1} - \begin{bmatrix} \Psi_{Hb} \\ \Psi_{HbO_2} \end{bmatrix}(L_b)^{-1} = \begin{bmatrix} [Hb]_b \\ [HbO_2]_b \end{bmatrix} \quad \text{(Eqn. 14)}$$

The parameters $A_{Hb}$ and $A_{HbO2}$ represent the product of the matrices $[\Delta A_\lambda]$ and $[\Delta\alpha']^{-1}$ and the parameters $\Psi_{Hb}$ and $\Psi_{HbO2}$ represent the product of the matrices $[\Delta E'_\lambda]$ and $[\Delta\alpha']^{-1}$. To determine the level of organ blood oxygen saturation ($StO_2$), Equation 14 is rearranged using the form of Equation 1 and is expressed as follows:

$$SnO_2\ \% = \frac{(A_{HbO_2} - \Psi_{HbO_2})}{(A_{HbO_2} - \Psi_{HbO_2} + A_{Hb} - \Psi_{Hb})} * 100\% \quad \text{(Eqn. 15)}$$

Note that the effective pathlength $L_b$ cancels out in the manipulation from Equation 14 to Equation 15.

The value for $StO_2$ is initially determined from $SmvO_2$ using Equation 4 and the empirically determined values for $SvO_2$ and $SaO_2$, determined from the organ to be monitored. The empirically determined values for $SvO_2$ and $SaO_2$ are based on data developed by discrete sampling (e.g., collections of blood sample at discrete points in time) or continuous monitoring (e.g., sensing blood flow through a catheter) of the subject's blood from the arterial input and venous output of the organ to be monitored, performed at or about the same time as the sensing of the organ tissue with the sensor. The temporal and physical proximity of the NIRS sensing and the development of the empirical data helps assure accuracy. For example, in calibrating the NIRS sensor to the heart, $SaO_2$ can be determined from blood in the aorta (arterial blood enters to coronary arties of the heart via the aorta) or any systemic artery. Heart $SvO_2$ will be determined from blood drawn from the coronary venous drainage of the heart. The initial values for Kv and Ka within Equation 4 are clinically reasonable values for the circumstances at hand. Alternatively, only $SvO_2$ may be used for empirical calibration (i.e., Ka=0, Kv=1). The values for $A_{HbO2}$ and $A_{Hb}$ are determined mathematically using the values for $I_{b\lambda}$ and $I_{x\lambda}$ for each wavelength sensed with the NIRS sensor (e.g., using Equation 5 and 6). The calibration parameters $\Psi_{Hb}$ and $\Psi_{HbO2}$, which account for energy losses due to scattering as well as other background absorption from biological compounds, are then determined using Equation 14 and non-linear regression techniques by correlation to different weighted values of $SvO_2$ and $SaO_2$; i.e., different values of Ka and Kv. Statistically acceptable values of Kv and Ka and $\Psi_{Hb}$ and $\Psi_{HbO2}$ are converged upon using the non-linear regression techniques. Experimental findings show that after proper selection of Ka and Kv, the calibration parameters $\Psi_{Hb}$ and $\Psi_{HbO2}$ are constant within a statistically acceptable margin of error for an individual NIRS sensor used to monitor direct organ oxygenation on different human subjects. In other words, once the sensor is calibrated it can be used on various human subjects and produce accurate information for each human subject for each organ type. The same is true for animal subjects.

In the determination of the $StO_2$ percentage, the effective photon pathlength $L_b$ cancels out. If, however, the photon pathlength is known or estimated, then the determination of the total value of Hb and/or $HbO_2$ is possible. For example, if a value for pathlength $L_b$ is input into Equation 14 along with the calibration values $\Psi_{Hb}$ and $\Psi_{HbO2}$, then the total value of Hb and/or $HbO_2$ can be calculated. According to Equation 2, pathlength L can be estimated from the product of "B*d". The light source to detector separation (optode) distance parameter "d" in the pathlength calculation is a measurable value and can be made constant by setting a fixed distance between light source to detector in the NIRS sensor design. Alternatively, the parameter "d" can be measured once the optodes are placed on the subject by use of calipers, ruler, or other distance measurement means. The pathlength differential factor "B" is more difficult to measure and requires more sophisticated equipment. An estimation of the value of "B" can be determined within a statistically acceptable margin of error for empirical data collected from subjects; e.g., a large data set of measured organ differential pathlength factor values. Substitution of these predetermined values of "B" into Equation 14 results in the determination of the total values of Hb and $HbO_2$.

After the calibration parameters $\Psi_{Hb}$ and $\Psi_{HbO2}$ are determined using the above-described methodology for an individual NIRS sensor, this particular sensor is said to be calibrated. A calibrated NIRS sensor affords accurate measurement of total tissue oxygen saturation, $StO_2$, by non-invasive means for each particular organ type. The calibrated sensor can be used thereafter on any human patient, including adults and neonates. The same is true for an animal subject if the sensor was calibrated on animals.

Besides Hb and $HbO_2$, other biological constituents of interest (e.g., cytochrome $aa_3$, etc.) could be determined using the multivariate forms of equations 2, 3, 6 or 7. For each additional constituent to be determined, an additional measuring wavelength will be needed.

In an alternative embodiment, the above-described methodology can be combined with pulse oximetry techniques to provide an alternative non-invasive method of distinguishing between oxygen saturation attributable to venous blood and that attributable to arterial blood. As demonstrated by Equation 4, $SmvO_2$ is determined by the ratio of venous oxygen saturation $SvO_2$ and arterial oxygen saturation $SaO_2$ from each particular organ type. A calibrated NIRS sensor affords accurate measurement of total tissue oxygen saturation, $StO_2$, by using regression techniques by correlation to mixed venous oxygen saturation $SmvO_2$. Therefore, the following expression will result:

$$StO_2 = SmvO_2 = K_v * SvO_2 + Ka * SaO_2 \quad \text{(Eqn. 16)}$$

Non-invasive pulse oximetry techniques can be used to determine the arterial oxygen saturation ($SaO_2$) of peripheral tissue (i.e. finger, ear, nose) by monitoring pulsatile optical attenuation changes of detected light induced by pulsatile arterial blood volume changes in the arteriolar vascular system. Arterial blood oxygen saturation determined by pulse oximetry is clinically denoted as $SpO_2$. If NIRS monitoring and pulse oximetry monitoring are done simultaneously and $SpO_2$ is set equal to $SaO_2$ in Equation 16, then venous oxygen saturation of a particular organ being monitored can be determined from the following expression:

$$SvO_2 = \frac{StO_2 - (Ka * SpO_2)}{Kv} \quad \text{(Eqn. 17)}$$

For the heart, venous oxygen saturation $SvO_2$ would be determined from the coronary drainage SvO2 and the parameters Ka and Kv would be empirically determined during the calibration of the NIRS sensor. Under most physiological conditions, $SpO_2$ is representative of organ arterial oxygen saturation $SaO_2$. Therefore, depending on which venous saturation parameter was used to calibrate the NIRS sensor, this clinically important parameter (organ venous oxygen saturation) can be determined by Equation 23 by non-invasive means.

To perform a corrective procedure (e.g., coronary artery bypass grafting, or heart valve replacement, or correction of congenital heart defect, etc.) on a subject's heart, it is often necessary to arrest or stop the subject's heart so that surgical procedures can be done in a still and bloodless field. In some instances this is achieved by diverting deoxygenated blood that would otherwise entering the heart into a heart-lung machine. The heart-lung machine takes over the function of the lung by oxygenating the blood and removing carbon dioxide. After oxygenation, filtration and removal of carbon dioxide, the machine pumps the blood back into the body usually through the aorta.

At the same time, the subject's heart is isolated, for example, using an aortic cross-clamp on the distal aorta. Cold cardioplegia is subsequently given into the heart through the aortic root. The cold fluid (usually in the range of about 4-10° C.) ensures that the heart cools down to an approximate temperature of around 15-20° C. thus slowing down the metabolism of the heart and thereby preventing damage to the heart muscle. The process may be further augmented by a cardioplegic component which is high in potassium and magnesium. The potassium helps by arresting the heart in diastole thus ensuring that the heart does not use up the valuable energy stores during this period of heart isolation. Blood can be added to this solution especially for long procedures requiring more than half an hour of cross-clamp time. Blood acts a buffer and also supplies nutrients to the heart during ischemia.

During the procedure (e.g., before, during, and after isolation), a sterile NIRS sensor is placed on a region of the heart. The sensor may have one or more detectors. The sensor is operated to transmit light signals into the heart tissue and receive light signals that have passed through the heart tissue. The oxygen saturation of the heart tissue is determined using the oximeter described above.

Using the present invention oximeter in the way described (or similar way) enables the physician to monitor the oxygen saturation level of the heart tissue and take corrective action (e.g., add a cardioplegic component) if the saturation reaches a predetermined level. The ability to place a sensor directly in contact with the heart during the procedure enhances the accuracy of the data, as there is no interfering tissue overlaying the heart, thereby providing the care giver with quick, concise information relation to the oxygenation state of the organ. In this manner, the operator can monitor in real-time the cardioplegia of the heart, including the rate of recovery from the cardioplegia.

Once the procedure on the heart (e.g., coronary artery bypass grafting, or heart valve replacement, or correction of congenital heart defect, etc.) is over, the cross-clamp is removed and the isolation of the heart is terminated so that normal blood supply to the heart is restored and the heart starts beating again. At this point, the oximeter can be used to confirm the oxygen saturation level within the heart tissue is within acceptable limits.

Figure 6:
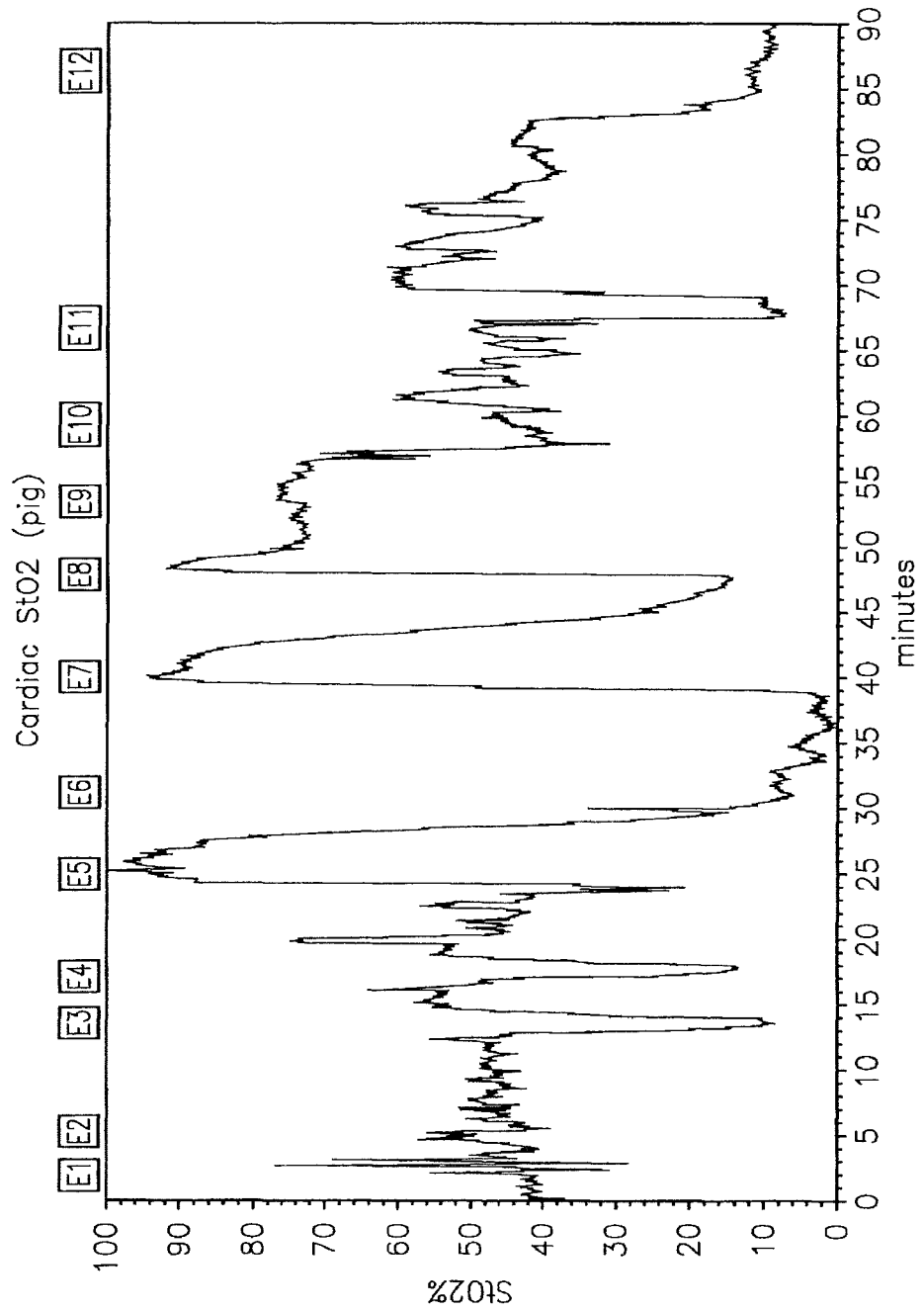
FIG. 6 graphically illustrates case study data in the form of $StO_2$ value versus time.

The utility of the present invention can be seen through the case study depicted in FIG. 6, which shows a recording of $StO_2$ from a present NIRS sensor placed directly on the heart of a pig. The events occurring during the study are identified to illustrate the relationship between a change in the level of $StO_2$ and the event encountered during the cardiac surgery. Event 1 ("E1") shows normal sinus rhythm. The $StO_2$ value for Event 1 is fairly low due to the high oxygen extraction of the heart muscle. Blood drawn from the venous return of the heart (carotid sinus) is typically highly oxygen de-saturated, with an oxygen saturation value around 40%. During Event 2 ("E2"), the pig was put on a cardiac bypass pump. During Event 3 ("E3"), a cross clamp was placed on the ascending aorta, proximal to the cardiopulmonary bypass ("CPB") inflow cannula. The cross clamp stopped blood flow to the heart; e.g., to allow a physician to perform surgery on the heart devoid of blood in the field. As a result, the $StO_2$ value decreased because the heart was no longer receiving oxygenated blood. Removal of the cross-clamp resulted in a resumption of blood perfusion to the heart, and the $StO_2$ value consequently increased back to pre-clamping $StO_2$ levels. Event 4 ("E4") was a repeat of Event 3. During Event 5 ("E5"), the cross-clamp was applied again, with a consequent decrease in the $StO_2$ level. Subsequently, cardioplegia was injected into the ascending aorta. The cardioplegia consisted of cooled (10 degrees C.) arterial blood and a saline-like solution, that included a relatively high level of potassium and other components such as adenin and Sodium (Na) channel blockers solution. The only vessels that extend out from the ascending aorta are the coronaries, provided that the aortic valve is competent. The infusion of cardioplegia into the ascending aorta passed through the coronary arteries. Since arterial blood is nearly 100% oxygenated, the cardiac NIRS sensor sensed a sharp rise in $StO_2$ level as the highly oxygenated blood perfused through the coronary vessels of the heart. The $StO_2$ level remained elevated for a few minutes as the heart muscle metabolizes the oxygen from the injected blood solution. Eventually all (or nearly all) the oxygen was extracted from the injected blood solution, causing the $StO_2$ level to decrease steadily until a value near zero was approached, which is depicted at Event 6 ("E6"). The $StO_2$ level remained near zero until a second dose of cardioplegia was administered—depicted at Event 7 ("E7"). The $StO_2$ level subsequently rose again to elevated values as the heart received freshly oxygenated blood solution from the second dose of cardioplegia. As the second dose of cardioplegia wore off, the $StO_2$ level decreased. This form of cardioplegia is referred to as antegrade cardioplegia. Another type of cardioplegia is called retrograde cardioplegia, which is injected into the coronary sinus of the heart to induce the same effect.

At Event 8 ("E8"), the cross-clamp was removed and the heart reperfused from systemic flow from the ascending aorta. At Event 9 ("E9"), the heart underwent ventricular fibrillation and arrhythmia Because the heart's contraction was uncoordinated and the cardiac muscles were not fully contracting, the oxygen consumption was reduced, resulting in a higher than normal cardiac $StO_2$ level. At Event 10 ("E10"), the heart was defibrillated to induce normal sinus rhythm, at which point the $StO_2$ level returned to a normal sinus rhythm value. Event 11 ("E11") illustrates a potential problem from blood pooling around the heart. The pooled blood negatively affected the ability of the NIRS sensor to accurately sense the $StO_2$ level within the heart. A NIRS cardiac sensor that is well adhered to the heart muscle can avoid this problem because it prevents outside blood leaking into the sensor's optical interface with the heart muscle. In one embodiment, the sensor can include a mechanism for inducing suction between the sensor and the surface of the heart; e.g., a syringe positioned to create suction can be used to create and maintain a seal that prevents outside blood leakage. At Event 12 ("E12"), the animal expired and the $StO_2$ level decreased to near zero values.

It can be seen from the above that the present apparatus for, and method of, directly monitoring the level of $StO_2$ in an organ using an NIRS sensor, provides an accurate and effective tool for directly monitoring both the $StO_2$ level of the organ and the affects of cardioplegia on the $StO_2$ level. Furthermore, the present invention provides the ability to regulate the $StO_2$ level within the organ using information collected during such monitoring. For example, the $StO_2$ level within a subject's heart can be directly monitored using the present invention during organ surgery (e.g., heart surgery). In one embodiment, the level of $StO_2$ is monitored and if the $StO_2$ level decreases beyond a predetermined minimum value threshold while the heart is cross-clamped, a predetermined dosage of cardioplegia is injected into the organ to cause the $StO_2$ level to increase above the threshold. It should be noted that the $StO_2$ threshold may be chosen based on the circumstances of the application; e.g., the threshold may be a value recorded during normal sinus rhythm and cardiac function, or some other clinically relevant value.

Figure 7:
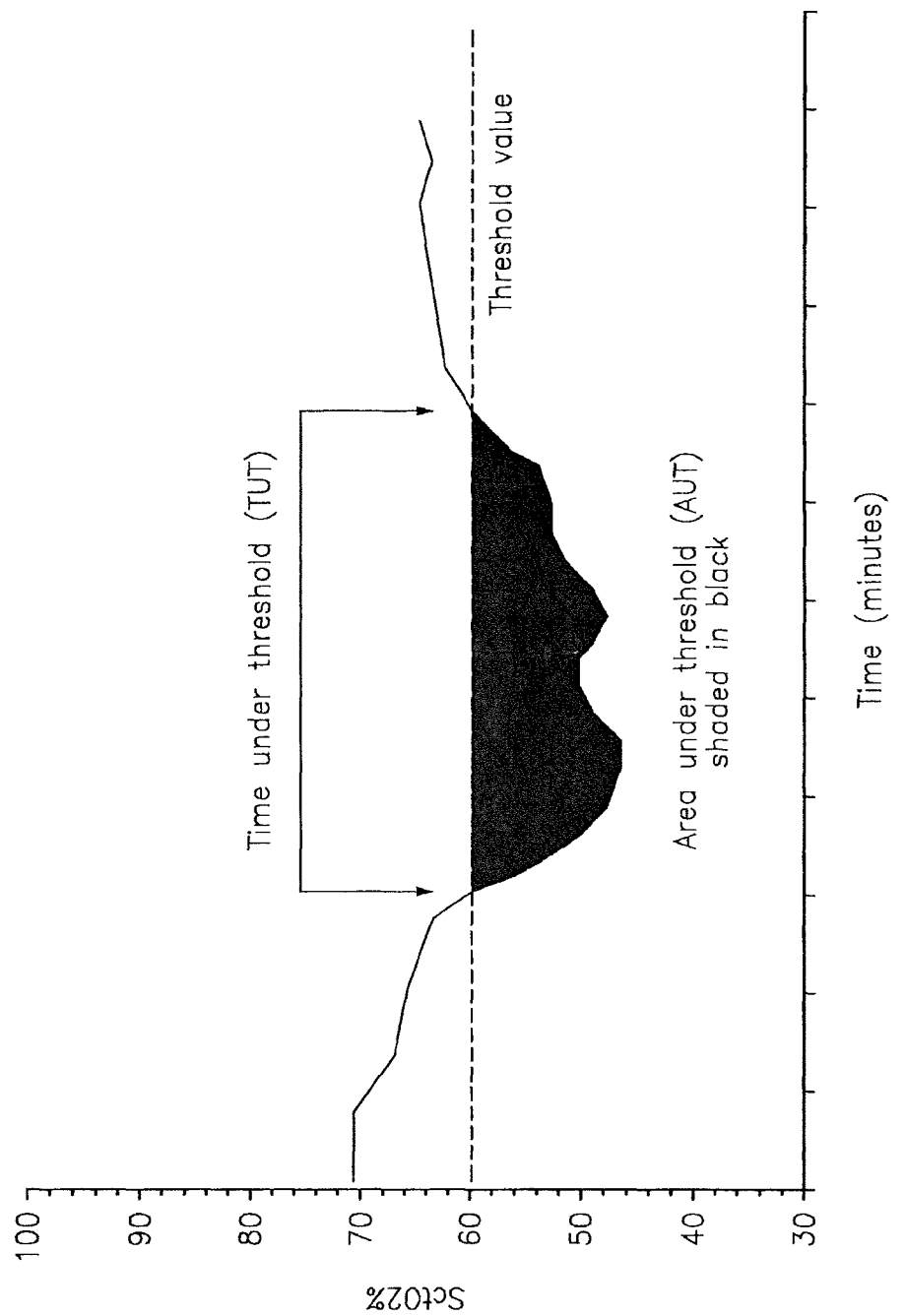
FIG. 7 is a graphical illustration depicting TUT and AUT regions.

In another embodiment, the $StO_2$ level is again monitored and the value of the $StO_2$ level is compared against a predetermined $StO_2$ level threshold as a function of time. For example, if the $StO_2$ level within the organ drops below the $StO_2$ threshold (referred to as an "event"), the amount of time that the $StO_2$ value is below the threshold (i.e., the duration of the event) is recorded and summed to create a time under threshold (i.e., "TUT") value (typically expressed in units of seconds or minutes). FIG. 7 graphically illustrates a TUT region. Anytime the $StO_2$ level exceeds the threshold, the TUT value remains constant and unchanged. The TUT value can then be compared to a threshold value for supplementary and/or corrective action if required.

The monitoring and collective summing relative to $StO_2$ values below the threshold can also be implemented (e.g., within the processor 12) graphically using a graph of $StO_2$ (e.g., Y-axis) versus time (e.g., X-axis). For example, if the comparison of the sensed $StO_2$ level with the predetermined $StO_2$ level reveals that the $StO_2$ level within the organ is below the threshold value, the area of the graph defined by the data line and the threshold value (i.e., from start of the event to the finish of the event) is calculated and summed to create an area under threshold (i.e., "AUT") value. FIG. 7 graphically illustrates an AUT region. Anytime the $StO_2$ level exceeds the threshold, the AUT value remains constant and unchanged. The AUT value can then be compared to a threshold value for supplementary action if required.

The area under $StO_2$ threshold ("AUT") value can also be calculated mathematically, where the AUT value (in units of $StO_2$%·time) is the accumulated oxygen saturation deficit below a threshold multiplied by time. AUT can be calculated, for example, using the following equation:

$$AUT = AUT_{past} + (StO_{2threshold} - StO_{2value}) \times \text{sample rate} \quad [\text{Eqn. 18}]$$

where AUT is the collective value, $AUT_{past}$ is the previous collective value, $StO_{2\ threshold}$ is the threshold value, and $StO_{2\ value}$ is the currently sensed $StO_2$ value. If the currently sensed $StO_2$ value is above the threshold, then the collective AUT value remains constant. The AUT is calculated for the entire procedure or just for one portion of the procedure (e.g., during a period of circulatory arrest). Because the $StO_2$ level of an organ will likely fluctuate during the course of an operation (i.e., $StO_2$ values above and below the predetermined threshold value), the AUT value can be periodically determined. To illustrate, consider the following monitoring using an arbitrary sample rate of sensing every five minutes and a $StO_2$ threshold value of 60): At a first point in time (T1), the AUT value may be considered to be zero (e.g., current sensing not yet started, and no past value of AUT). Five minutes later at T2, the $StO_2$ of the organ is sensed and has a value of 58. Using Eqn. 1 above, the AUT value is calculated: $[(0+(60-58)\times5=10]$, because there is no $AUT_{past}$ value, and it is therefore assigned a value of zero. Five minutes later at T2, the StO2 of the organ is sensed and has a value of 57. Again using Eqn. 1: $[((60-57)\times5)+10=25]$, because the $AUT_{past}$ value is equal to ten. Five minutes later at T3, the $StO_2$ of the organ is sensed and has a value of 63. In this instance, because the sensed $StO_2$ value is greater than the threshold, the difference is assigned a value of zero, and the AUT value remains at twenty-five, because the $AUT_{past}$ value is equal to twenty-five.

It should be noted that the AUT value is not a percentage of time spent under a given threshold, but rather is an absolute value that can be used during or after the procedure as part of the subject's care; e.g., depending upon the application, there may be little difference in clinical terms between a collective $StO_2$ duration of one hour underneath a threshold during a 10 hour case (10%) as opposed to a collective one hour during a one hour case (100%).

It can be seen from the description above, including the various different embodiments, that the present invention provides a method and apparatus for monitoring cardioplegia. The present invention can be used to protect the subject's heart (or other organ), by alerting the physician to take a proactive step (e.g., inject the next round of cardioplegia) when certain predefined conditions are met. The present method can be utilized in varying degrees of automation (e.g., algorithmically within the processor 12), including an automated cardioplegia device that includes structure adapted to automatically inject cardioplegia based on NIRS $StO_2$ monitoring input.

As indicated above, the present apparatus and method can be used to directly monitor numerous organs within a subject's body and is not, therefore, limited to a cardiac application. For example, the present invention can be used to monitor oxygenation levels within a liver or kidney allograft before, during and after transplantation. Issues may arise during transplantation such as reconnect of blood vessels that feed the organ, as well as preventing hyperoxygenation and reperfusion injury. An NIRS organ sensor could be moved to different positions on the organ to make sure each region or compartment is perfused adequately. This is especially true with liver transplantation. To prevent hyperoxygenation and in part, reperfusion injury, the organ $StO_2$ can be controlled by observing the NIRS monitor $StO_2$ value and then regulating blood flow or the oxygenation level so that $StO_2$ is maintained within a predetermined range during transplant. Specifically, a sterile NIRS sensor is placed on a region of the liver or kidney allograft. Secure attachment of the sensor can be made by suction means or by suturing the sensor onto the organ. Alternatively, a loose wrapping over the sensor to hold it on the organ, such as a stretchable net-like apparatus can be used. Although the sensor may have one or more detectors, the direct sensing of the organ typically permits the use of a single detector sensor since attenuation attributable to non-organ tissue layers is avoided. The sensor is operated to transmit light signals into the liver tissue and receive light signals that have passed therethrough. The oxygen saturation of the liver tissue is determined using the oximeter described above. As indicated above, the direct organ monitoring made possible using the present invention enables the physician to accurately monitor the organ and take corrective action as needed.

Since many changes and variations of the disclosed embodiment of the invention may be made without departing from the inventive concept, it is not intended to limit the invention otherwise than as required by the appended claims.

What is claimed is:

1. A method for non-invasively determining a blood oxygen saturation level within tissue of an internal organ of a subject, comprising:

applying a near infrared spectrophotometric sensor on an external surface of the internal organ, which sensor includes at least one light source and at least one detector;

operating the sensor to emit light from the light source at an incident light intensity directly into the tissue of the internal organ at a first tissue location, which emitted light includes a plurality of wavelengths, and to sense said emitted light at a second tissue location, separated from the first tissue location, which emitted light has traveled through the tissue between the first tissue location and the second tissue location, and to produce signals representative of the intensity of the sensed emitted light;

using a processor to execute instructions stored in a memory device, which instructions cause the processor to:

determine an attenuation value of the emitted light for each of the plurality of wavelengths using a first value representative of the incident light intensity for the respective wavelength and a second value representative of the intensity of the sensed emitted light for the respective wavelength; and determine a blood oxygen saturation level of the organ tissue using the determined attenuation values for each of the plurality of wavelengths.

2. The method of claim 1, wherein the sensor applied to the external surface of the organ is configured to interrogate tissue contiguous with the external surface of the organ.

3. The method of claim 2, wherein the sensor has a plurality of light detectors.

4. The method of claim 2, wherein the sensor is configured to be applied to the external surface of a heart and to interrogate tissue contiguous with the external surface of the heart.

5. The method of claim 2, wherein the sensor is configured to be applied to the exterior surface of a liver and to interrogate tissue contiguous with the external surface of the liver.

6. The method of claim 2, wherein the sensor is configured to be applied to the external surface of a kidney and to interrogate tissue contiguous with the external surface of the kidney.

7. The method of claim 1, wherein the at least one detector is spaced a distance apart from the light source, and wherein the distance is such that the sensed emitted light travels substantially exclusively through the organ tissue.

8. The method of claim 1, wherein the at least one detector includes a first detector spaced a first distance apart from the light source, and a second detector spaced a second distance from the light source, which second distance is greater than the first distance, and wherein the first and second distances are such that the sensed emitted light travels substantially exclusively through the organ tissue.

9. The method of claim 1, wherein the instructions stored in the memory device include a predetermined organ tissue oxygenation level threshold and which instructions further cause the processor to compare the predetermined organ tissue oxygenation level threshold and the determined blood oxygen saturation level of the organ tissue.

* * * * *